United States Patent
Killmer et al.

(10) Patent No.: US 10,806,150 B2
(45) Date of Patent: *Oct. 20, 2020

(54) METHODS AND COMPOSITIONS OF INSECT CONTROL

(71) Applicant: APSE, INC., St. Louis, MO (US)

(72) Inventors: John L. Killmer, St. Louis, MO (US); Juan Pedro Humberto Arhancet, St. Louis, MO (US); Patrick D. McLaughlin, St. Louis, MO (US)

(73) Assignee: APSE, INC., St. Lois, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,097

(22) PCT Filed: Dec. 7, 2016

(86) PCT No.: PCT/US2016/065408
§ 371 (c)(1),
(2) Date: Jun. 13, 2018

(87) PCT Pub. No.: WO2017/116644
PCT Pub. Date: Jul. 6, 2017

(65) Prior Publication Data
US 2018/0368422 A1    Dec. 27, 2018

Related U.S. Application Data

(60) Provisional application No. 62/273,654, filed on Dec. 31, 2015.

(51) Int. Cl.
| C07H 21/04 | (2006.01) |
| A01N 63/00 | (2020.01) |
| C07K 14/005 | (2006.01) |
| C12N 15/113 | (2010.01) |
| C12N 15/70 | (2006.01) |
| C12N 15/81 | (2006.01) |

(52) U.S. Cl.
CPC ............ *A01N 63/00* (2013.01); *C07K 14/005* (2013.01); *C12N 15/113* (2013.01); *C12N 15/1131* (2013.01); *C12N 15/70* (2013.01); *C12N 15/81* (2013.01); *C12N 2310/14* (2013.01); *C12N 2770/00042* (2013.01); *C12N 2795/16023* (2013.01); *C12N 2795/18023* (2013.01)

(58) Field of Classification Search
None
See application file for complete search history.

(56) References Cited

U.S. PATENT DOCUMENTS

| 2013/0017210 A1 | 1/2013 | Peabody et al. |
| 2015/0322455 A1 | 11/2015 | Narva et al. |

OTHER PUBLICATIONS

Tars, Kaspars, et al. "The crystal structure of bacteriophage GA and a comparison of bacteriophages belonging to the major groups of *Escherichia coli* leviviruses." Journal of molecular biology 271.5 (1997): 759-773.*
International Search Report of PCT/US2016/065408 dated Apr. 28, 2017.
Written Opinion of PCT/2016/0605408 dated Apr. 28, 2017.
Palli, S., "RNA Interference in Colorado Potato Beetle: Steps Toward Development of dsRNA as a Commercial Insecticide," Curr. Opin. Insect. Sci., vol. 6, pp. 1-8 (Dec. 2014).

* cited by examiner

*Primary Examiner* — Kimberly Chong
(74) *Attorney, Agent, or Firm* — Polsinelli PC; Tara A. Nealey

(57) ABSTRACT

The invention describes recombinant DNA sequences transcribed into RNA constructs capable of forming Virus Like Particles (VLPs) suitable for insect control applications. Specifically, the disclosure provides a method for controlling target insects comprising, transforming a microbial host with a first DNA sequence comprising a gene encoding a bacteriophage capsid protein and a second DNA sequence encoding an RNA transcript comprising at least one bacteriophage pac sequence coupled to an RNAi precursor sequence, inducing the microbial host to express the first and second DNA sequences, isolating virus-like-particles (VLPs) comprising the capsid protein and RNAi precursor from the microbial host, and contacting the isolated VLPs with the target insects.

10 Claims, No Drawings

Specification includes a Sequence Listing.

METHODS AND COMPOSITIONS OF INSECT CONTROL

CROSS REFERENCE TO RELATED APPLICATIONS

This application claims priority to U.S. provisional application No. 62/273,654, filed Dec. 31, 2015, the entire disclosure of which is incorporated by reference.

INCORPORATION OF SEQUENCE LISTING

The entire contents of a paper copy of the "Sequence Listing" and a computer readable form of the sequence listing entitled Insect_Control_Sequence_Listing ST25.txt, which is 27 kilobytes in size and was created on Dec. 7, 2016, are herein incorporated by reference.

FIELD OF THE INVENTION

The invention comprises methods and compositions relating to virus-like particles (VLPs) containing heterologous cargo molecules capable of generating an RNAi-mediated gene suppression effect on targeted insects. Such compositions and methods have application in crop protection and other aspects of insect control.

BACKGROUND OF THE INVENTION

RNAi-mediated gene suppression, first described in the nematode *C. elegans*, has been shown to be an effective method for modulating gene expression in many other organisms. Fire, et al., *Potent and specific genetic interference by double-stranded RNA in Caenorhabditis elegans.* Nature 391:806 (1998). The role of RNAi in controlling proliferation of insects affecting crops has been demonstrated using double-stranded RNA (dsRNA) by a number of research groups. Reviewed in, Ivashuta, et al. *Environmental RNAi in herbivorous insects.* RNA 21:840 (2015). Recombinant RNA constructs used for RNAi purposes described in the prior art generally consist of dsRNAs of about 18 to about 25 base pairs (siRNAs), but also include longer dsRNAs (long dsRNAs) usually between about 100 to about 1,000 base pairs (bp). To successfully introduce dsRNA into insects, dsRNAs longer than or equal to approximately 60 bp are required for efficient uptake when supplied in the insect's diet. Bolognesi, et al. *Ultrastructural Changes Caused by Snf7 RNAi in Larval Enterocytes of Western Corn Rootworm (Diabrotica virgifera virgifera Le Conte)* PLoS One 7:e47534 (2012). Long dsRNA molecules are cleaved in-vivo into a diverse population of siRNAs by the host's Dicer enzyme complex. Alternatively, RNAi gene suppression can also occur through the action of anti-sense RNAs directed to specific sequences via related processes. Practical application of RNAi methods for controlling insects in the field is limited by the cost of in vitro RNA synthesis and the chemical fragility of RNA, even dsRNAs, to environmental and enzymatic degradation.

Bacteriophage MS2 capsid mediated delivery of toxins and imaging agents to human cancer cells has been shown to be an effective method for delivering such agents to eukaryotic cells in vitro. Ashley, et al., *Cell-specific delivery of diverse cargos by bacteriophage MS2 virus-like particles.* ACS nano 5:5729 (2011). Whether such bacteriophage capsids can serve a similar function for delivery of RNAi precursors to insects in the field is unknown. Effective delivery of RNAi precursors into target insects requires preventing non-specific RNA degradation, a facile route of administration, and the ability to release the RNAi precursors at the appropriate point within the target insect such that the RNAi precursors can be taken up by the insect cells and properly processed. Ideally, the RNAi precursor and delivery system must be economical and relatively simple to produce and distribute. The inventions described here satisfy all these criteria and have the added benefit of allowing rapid discovery, prototyping and commercial-scale production of new RNAi molecules.

SUMMARY OF THE INVENTION

The invention described here uses the unique properties of VLPs, (alternatively known as APSE RNA Containers, or "ARCs"), to provide an improved system for delivering long dsRNA and RNAi precursors (dsRNAi) which can be processed intra-cellularly to produce siRNA for suppressing expression of a target gene, preferably in an insect host, more preferably a Coleopteran or Lepidopteran insect pest. Of particular interest are Coleoptera such as bark beetle, elm leaf beetle, Asian longhorn beetle, death watch beetle, mountain pine beetle, coconut hispine beetle, the various corn rootworms and the Colorado potato beetle. RNAi methods of controlling Colorado potato beetle are especially desired since these beetles have developed resistance to virtually all known insecticides.

Coleopteran insect pests are known to be susceptible to RNAi introduced via the gut, either by direct injection or by feeding on plant matter treated with RNAi precursors. Field application of naked RNAs is generally impractical due to the sensitivity of RNA to environmental specific and non-specific degradation. Furthermore, RNA is highly susceptible to degradation during the course of feeding and in transit through the insect gut. The highly stable form of VLPs serves to protect RNA borne within the VLPs in vitro. The question remains, are VLPs capable of effectively delivering RNAi precursors to the RNAi processing pathways, such as Dicer, of target insects? In particular, can VLPs protect RNAi precursors within the insect digestive tract and still deliver the intact RNAi precursor to the RNAi processing pathway of the target insect? The results presented here indicate that VLPs are extremely effective at delivering RNAi precursors into target insects.

An important advantage of producing RNAi precursors by the methods described here is that costly and complicated in vitro synthesis of RNA precursors is avoided and the desired RNA constructs can be produced by simple and economic fermentation methods. Production and purification of large quantities of RNAi precursors is facilitated by optionally coupling synthesis of the desired polynucleotide with expression of self-assembling bacteriophage capsid proteins, such as those of bacteriophage Qβ or MS2 to produce easily purified and relatively stable ARCs (VLPs), which may be applied directly to plant surfaces upon which the targeted insect pests feed, for example by spraying.

Once ingested, the ARCs may be digested in the course of transiting the insect host gut and the RNA molecules absorbed by cells lining the gut. Within the target insect cells the RNAi precursors are processed by, among other things, the host Dicer enzyme complex to generate effective RNAi forms targeted against host gene transcripts to suppress expression of essential host genes. Examples of such essential genes include, without limitation, genes involved in controlling molting or other larval development events, actin or other cellular structural components, as well as virtually any gene related to replication, transcription or translation or other fundamental process required for viability.

DETAILED DESCRIPTION OF THE INVENTION

The present invention comprises DNA sequences, which when transcribed produce RNAi precursor molecules and mRNA translated into bacteriophage coat protein, which together, are incorporated into uniquely stable VLPs. The VLPs may be purified in a form suitable for ingestion by feeding insects. Once ingested by the target insects, the VLPs transit the gut where they are then assimilated into the insect cells where the RNAi precursor is processed into a form of RNAi that suppresses expression of a target gene important to insect viability. In some embodiments, suppression of such target genes is designed to result in death of the target insect. In another embodiment suppression of target genes is designed to produce sterile off-spring. A key feature of the VLPs is that they are stable enough to protect the encapsidated RNAi precursors from degradation by non-specific environmental agents or by insect target cell RNAse enzymes, but remain capable of introducing the RNAi precursors into the RNAi pathways in target insect cells after they are ingested.

Example sequences presented here are designed to be ligated into suitable bacterial plasmid vectors as AsiSI-NotI digested DNA fragments. Such DNA sequence fragments can be produced by direct synthesis or by sub-cloning the constituent fragments using techniques well known to those skilled in the art. The specific sequences may be modified as desired to manipulate specific restriction enzyme sites, incorporate alternative ribozyme binding sites, accommodate alternative bacteriophage pac sequences and the specificity of the RNAi sequences may be modified to target different genes and insect hosts. Bacterial plasmid vectors containing transcriptional promoters capable of inducibly transcribing these DNA sequences include without limitation, bacteriophage T7 gene 1 promoter, bacteriophage T5 promoter and the bacteriophage lambda $P_L$ and $P_R$ promoters. Bacterial plasmid vectors may also contain the bacteriophage Qβ or bacteriophage MS2 capsid protein coding sequence expressed from an inducible promoter. Alternatively, such inducibly expressed capsid proteins may be present on a separate bacterial plasmid compatible with the bacterial plasmid carrying the inducible cargo RNA sequences.

The production and purification of VLPs containing RNA cargo molecules and recovery of the RNA cargo molecules are described in detail in U.S. Patent Application Publication Nos. 2013/0208221 (at least paragraphs 0013 and 0014), 2014/0302593 (at least paragraphs 0016, 0052, 0065 and 0085-0086) and as described in U.S. Pat. No. 9,181,531 (passim), the contents of each incorporated herein by reference. In addition, related methods are also described in U.S. Patent Application Publication Nos. 2010/0167981 and 2012/0046340, PCT/US2012/071419 and PCT/US2014/041111, and U.S. Pat. Nos. 5,443,969, and 6,214,982, the contents of each are also incorporated herein by reference. The VLPs produced by these methods can be processed in a number of different ways known to those skilled in the art to facilitate application of such material onto plants and for use in the field. In one embodiment the purified ARCs are further processed for spraying operations. Such processing may include spray drying, introduction of stabilizing or wetting agents or forming an admixture of VLPs with other desired agents prior to application. Field applications may involve ground or arial spray methods or spot application.

A person skilled in the art will understand that the invention may be targeted to different genes in different insect hosts by modifying the sequences from those described in the Examples to reflect the sequences of the targeted genes in the targeted host organisms. Thus, the invention provides those skilled in the art with a tool for determining the best RNAi target for suppressing a particular gene in any given host cell and a means for producing large quantities of such RNAis. Further, the invention provides for methods of empirically determining which gene or group of genes may constitute the most effective RNAi target within a single insect or group of insects by screening the effectiveness of VLPs containing various RNAi precursors targeted to specific genes or gene combinations in such insects by combinatory cloning methods. The invention also supports methods combining VLPs effective for control of certain insects in the field with different VLPs effective for control of other insects at the point of application, in order to tailor the insect control properties to those relevant at the point of application. The different insects may be of a different order, genus or species as those targeted by the original VLPs, or may comprise RNAi resistant, or combinations of RNAi resistant populations, wherein the combination of one or more VLPs targeting different genes within the target insect population ensures that no combination of RNAi resistance is likely to occur.

In one embodiment of the present invention, a first DNA sequence within a bacterial host is transcribed to produce a first RNA molecule encoding a bacteriophage coat protein, and a second DNA sequence within said bacterial host is transcribed to produce a second RNA molecule comprising a bacteriophage pac site, followed by an antisense sequence of a target gene from an insect, followed by a unique RNA sequence capable of forming a single-stranded loop, followed by a sense sequence complementary to the antisense sequence of the target gene sequence, followed by a second bacteriophage pac site. The first RNA molecule is an mRNA which is translated by the bacterial host to produce a plurality of bacteriophage coat protein which, in combination with the second RNA molecule comprising the bacteriophage pac sequences, spontaneously forms a VLP, wherein the second RNA molecule is packaged within the VLP. VLPs are isolated and purified prior to application to the outer surfaces of a plant. Target insects feeding upon the plant ingest the VLP which in turn introduces the RNA molecule borne within the VLP into the host insect cells where it is processed by the host insect cell's endogenous RNAi pathways, resulting in RNAi-mediated suppression of gene expression of the host insect target gene. In one embodiment the insect is of the order Coleoptera. In preferred embodiments the Coleopteran insect is a Colorado potato beetle.

In another embodiment of the present invention, a first DNA sequence within a bacterial host is transcribed to produce a first RNA molecule encoding a bacteriophage coat protein, and a second DNA sequence within said bacterial host is transcribed to produce a second RNA molecule comprising a bacteriophage pac site, followed by an antisense sequence of a target gene from an insect, optionally followed by one or more bacteriophage pac sites. The first RNA molecule is an mRNA which is translated by the bacterial host to produce a plurality of bacteriophage coat protein which, in combination with the second RNA molecule comprising the bacteriophage pac sequences, spontaneously forms VLPs, wherein the second RNA molecule is packaged within the VLP. The VLPs are isolated and purified prior to application to the outer surfaces of a plant. Target insects feeding upon the plant ingest the VLP which in turn introduces the RNA molecule borne within the VLP into the host insect cells where it results in anti-sense RNA-mediated suppression of gene expression of the host insect target gene. In one embodiment the insect is of the order Coleoptera. In preferred embodiments the Coleopteran insect is a Colorado potato beetle.

In another embodiment, a series of host bacteria containing a first DNA sequence encoding a bacteriophage coat protein and different second DNA sequences encoding various RNAi sequences are isolated. Each isolated host bacteria is clonally expanded and bacterial cell line archived. A sample of each bacterial cell line is subsequently outgrown and induced to transcribe the first and second DNA sequences, the VLPS are allowed to assemble within the host bacteria and the VLPs isolated therefrom. The RNA sequences within the series of resulting VLPs each encode a different antisense and optionally a complementary sense sequence homologous to different insect target genes or on different regions of a given insect target gene or on target genes from different insect targets altogether. Each of the different VLPs produced by the series of host bacteria is fed to target insects and their ability to suppress host insect gene expression is measured, for example by scoring target insect mortality. Those VLPs producing the greatest level of RNAi-mediated suppression of gene expression represent the most effective RNA target for that particular target insect or position within a given target insect gene. Recourse to the corresponding bacterial cell line that produced each VLP allows quick identification of the corresponding target sequence or gene. Likewise, recourse to the corresponding host bacterial cell line facilitates rapid scale-up of the desired VLP for RNAi-mediated suppression of gene expression of the host insect target gene for field application or further experimental investigation. One skilled in the art will recognize that random or pseudo-random collections of complementary DNA sequences based on insect genomic sequence data or for subsets of such genomic sequence encoding likely essential genes can be screened using multiplex or automated cloning technologies.

The following Examples are illustrative of the invention and are not intended to limit the scope of the invention as described in detail above and as set out in the appended claims.

EXAMPLE 1

Efficacy of Colorado Potato Beetle Control by VLPs Containing an RNAi Precursor To determine whether VLPs containing a dsRNAi precursor targeting the (β-actin gene of Colorado potato beetle (another Coleopteran insect) can suppress β-actin expression as effectively as the naked dsRNAi precursor, the following study was carried out. A 294 bp fragment of beta actin from Colorado potato beetle (*Leptinotarsa decemlineata* strain Freeville actin mRNA, GenBank sequence ID: gb|KJ577616.1, nucleotides 1-294) was cloned into pAPSE10136 (SEQ ID NO: 1) in such a way as to produce a transcript with sequences comprising both corresponding sense and anti-sense strands separated by a short loop of non-homologous sequence. This RNA represents a 294 bp dsRNAi precursor targeted against beta actin. The dsRNAi precursor DNA sequence was produced by PCR amplification of the 294 bp region of interest from Colorado potato beetle chromosomal DNA using primers 1174 (SEQ ID NO: 2) and 1175 (SEQ ID NO: 3), the PCR product was ligated into an intermediate plasmid by digestion of the PCR fragment and vector with restriction endonucleases AsiSI and PmeI in the sense orientation relative to one of the vector encoded T7 gene 1 promoter. The loop and anti-sense sequences were produced from the sense-strand DNA fragment by PCR amplification with primers 1213 (SEQ ID NO: 4) and 1203 (SEQ ID NO: 5). The resulting PCR fragment and the intermediate plasmid were digested with PmeI and RsrII and ligated together. The desired recombinant plasmids encoding the (β-actin sense and antisense strand sequences connected by a short linker expressed from a T7 gene promoter were identified by restriction digest screening. The desired plasmid, pAPSE10216 (SEQ ID NO: 6) was transformed into chemically competent HTE115 (DE3) cells and individual clones selected for ampicillin resistant transformants.

Ampicillin resistant transformants were selected on LB agar plates containing 100 micrograms/ml ampicillin. The selected clones were subsequently grown at 37° C. in 100 ml of LB media containing ampicillin until the culture reached OD600 0.8, at which time isopropyl β-D-thiogalactopyranoside was added to a final concentration of 1 mM to induce T7 polymerase directed transcription of MS2 capsid protein and the 294 bp siRNA precursor. The induced cultures were allowed to grow for at least 4 hours post-induction to allow sufficient time for VLP formation. Cells were collected by centrifugation at 3,000 g at 4 C. Each pellet was stored at 4° C. until processing.

VLPs containing the 294 bp siRNA precursor were purified by re-suspending each pellet in approximately 10 volumes of 20 mM Tris-HCl, pH 7.0, containing 10 mM NaCl and sonicated to lyse the cells. Cell debris was removed by centrifugation at 16,000 g. Each sample was further processed by addition of Benzonase® Nuclease (Sigma Aldrich, St. Louis, Mo.) added to a final concentration of about 100 units per mL and incubated at 37° C. for two hours. Proteinase K was then added to final concentration of 150 micrograms per mL and incubated at 37° C. for an additional three hours. A saturated ammonium sulfate solution was prepared by adding ammonium sulfate to water to a final concentration of 4.1 M. The saturated ammonium sulfate was added to the enzymatically treated VLPs to a final concentration of 186 mM (approximately a 1:22 dilution) and placed on ice for two hours. Unwanted precipitate was cleared from the lysate by centrifugation at 16,000 g. A second precipitation was conducted by addition of 155 mg of dry ammonium sulfate directly to each mL of cleared lysate. Each sample was vortexed and incubated on ice for two hours. Each precipitate was spun down at 16,000 g and the solid precipitate resuspended in one tenth the original volume of 20 mM Tris-HCl, pH 7.0, containing 10 mM NaCl.

The resuspended VLPs were used to test the efficacy of encapsidated RNAi on Colorado potato beetle larvae relative to the corresponding naked RNAi. Each experimental and control cohort included 10 individual beetles undergoing 10 identical treatments. Each treatment or control sample was applied in 50 μl droplets to the surface of a 1 cm diameter potato leaf disc. Each time an application was made, a clean pipette tip was used. The treatment was allowed to dry on the leaf surface prior to being presented to the larvae. During a pretreatment period, all food was removed from the larval containers and larvae were starved for 2 hours before introduction of treated leaves to the larvae. After the starvation period, one larva was placed on each treated potato leaf in a petri dish, where it was allowed to feed on the disc until the leaf tissue was completely devoured. Larvae were allowed to feed at three separate times on treated potato leaves every two days, given a normal diet of potato leaves in the interim and monitored for mortality on a daily basis up to 21 days post treatment. After the final treatment, live larvae were maintained on untreated potato leaves for an additional 21 days.

Table 1 summarizes the results of treating Colorado potato beetle larvae with the test RNAi administered as naked RNA or encapsidated in an ARC, produced from pAPSE10216. In addition, VLPs containing random *E. coli* derived RNAs with no significant homology to the Colorado potato beetle beta-actin were included as a control of general non-specific VLP toxicity. These results indicate that these VLP encapsidated RNAs are as effective in killing Colorado potato beetle larvae by suppressing expression of the essential actin gene as unencapsidated RNAi:

TABLE I

Summary of mortality rates for Colorado potato beetle (*Leptinotarsa decemlineata*) larvae treated with RNA and VLP formulations.

| Treatment | Dose (microgram) | Maximum mortality (%) | Days to reach maximum mortality |
|---|---|---|---|
| Untreated control | 0 | 20 | 15 |
| Water control | 0 | 20 | 16 |
| VLPs with unrelated dsRNA | 0.5 | 30 | 19 |
| VLPs with dsRNAi precursor | 0.5 | 100 | 1 |
| dsRNAi precursor without VLP | 0.5 | 100 | 1 |

The naked dsRNA treated controls exhibit a high degree of mortality, consistent with the hypothesis that suppression of actin gene expression by this dsRNA results in death of beetle larvae that consume it. The cohort treated with VLPs containing the unrelated RNA exhibit little or no mortality, indicating that VLPs are not inherently toxic to the beetle larvae. The ARCs provide an effective delivery platform for RNAi active molecules and the high level of mortality verifies that the packaging and processing steps for manufacturing VLPs does not inhibit effectiveness of the RNAi response observed from such dsRNA.

Additional experiments at doses lower than 0.5 μg, e.g. at 0.05 μg, reveal that ARCs with actin hairpin RNA have similar efficacy at lower doses to naked dsRNA at higher doses targeting the same actin sequence.

The ability of these constructs to kill Colorado potato beetle larvae confirms that these ARCs are an effective tool for introducing targeted RNAi precursors into an insect host and that these precursors can be properly processed by the host cell RNAi pathway to suppress gene expression of the target gene. These results directly demonstrate that ARCs comprising siRNA precursors are an effective delivery system for controlling Colorado potato beetle and Coleopteran insects generally.

EXAMPLE 2

Efficacy of Controlling Colorado Potato Beetle Larvae by VLPs Containing Single Stranded Antisense RNA To test whether anti-sense RNA (ssRNAi) can be effectively delivered to target insects by use of VLPs, a 294 bp DNA sequence fragment corresponding to a portion of the beta actin gene of Colorado potato beetle (*Leptinotarsa decemlineata* strain Freeville actin mRNA, GenBank sequence ID: gb|KJ577616.1, nucleotides 1-294) was constructed from primers 1176 (SEQ ID NO: 7) and 1177 (SEQ ID NO: 8). The primers were ordered from IDT (Integrated DNA Technologies, Inc., Coralville, Iowa) and used to amplify the beta actin sequence fragment from Colorado potato beetle genomic DNA by Accuprime PCR while adding an AsiSI restriction site 5' of the beta actin sequence fragment and a PmeI restriction site 3' of the beta actin sequence fragment. The resulting PCR product was digested with AsiSI and PmeI restriction endonucleases and subsequently ligated into pAPSE10136 (SEQ ID NO: 1) previously treated with AsiSI and PmeI, in the anti-sense orientation relative to the upstream T7 promoter, to form pAPSE10190 (SEQ ID NO: 9). This plasmid allows the (β-actin antisense strand RNA (ssRNAi) to be packaged in VLPs at high efficiency by incorporating bacteriophage pac sites into the transcript. Chemically competent HTE115 (DE3) cells were transformed and VLPs were produced by fermentation and subsequently isolated as described in Example 2. The VLPs were then tested for the ability to suppress Colorado potato beetle larvae as described in Example 2. Table 2 summarizes the results:

TABLE 2

Summary of mortality rates of Colorado potato beetle (*Leptinotarsa decemlineata*) larvae treated with single stranded anti-sense RNA and VLP formulations.

| Treatment | Dose (microgram) | Maximum mortality (%) | Days to reach maximum mortality |
|---|---|---|---|
| Untreated control | 0 | 20 | 15 |
| Water control | 0 | 20 | 16 |
| VLPs with no ssRNAi | 0.5 | 30 | 19 |
| VLPs with ssRNAi | 0.5 | 100 | 1 |
| ssRNAi without VLP | 0.5 | 100 | 8 |

These data indicate that VLPs improve the efficacy of single-stranded anti-sense RNA directed to suppressing expression of the essential beta-actin gene in killing Colorado potato beetle larvae. Further, these results indicate that these VLPs are even more effective in killing Colorado potato beetle larvae by suppressing expression of the essential actin gene than the corresponding unencapsidated RNAi. These results suggest that ARCs comprising antisense ssRNA also serve as an effective delivery system for controlling Coleopteran insects generally, and Colorado potato beetle specifically.

SEQUENCE LISTING

<160> NUMBER OF SEQ ID NOS: 9

<210> SEQ ID NO 1

```
<211> LENGTH: 5317
<212> TYPE: DNA
<213> ORGANISM: Artificial Sequence
<220> FEATURE:
<223> OTHER INFORMATION: plasmid pAPSE 10136
<220> FEATURE:
<221> NAME/KEY: misc_feature
<222> LOCATION: (213)..(230)
<223> OTHER INFORMATION: T7 promoter
<220> FEATURE:
<221> NAME/KEY: misc_feature
<222> LOCATION: (317)..(335)
<223> OTHER INFORMATION: MS2 bacteriophage PAC sequence
<220> FEATURE:
<221> NAME/KEY: misc_feature
<222> LOCATION: (365)..(372)
<223> OTHER INFORMATION: AsiSI restriction site
<220> FEATURE:
<221> NAME/KEY: misc_feature
<222> LOCATION: (426)..(433)
<223> OTHER INFORMATION: AscI restriction site
<220> FEATURE:
<221> NAME/KEY: misc_feature
<222> LOCATION: (454)..(460)
<223> OTHER INFORMATION: RsrII restriction site
<220> FEATURE:
<221> NAME/KEY: misc_feature
<222> LOCATION: (481)..(488)
<223> OTHER INFORMATION: NotI restriction site
<220> FEATURE:
<221> NAME/KEY: misc_feature
<222> LOCATION: (511)..(518)
<223> OTHER INFORMATION: PacI restriction site
<220> FEATURE:
<221> NAME/KEY: misc_feature
<222> LOCATION: (528)..(546)
<223> OTHER INFORMATION: MS2 bacteriophage C-PAC sequence
<220> FEATURE:
<221> NAME/KEY: misc_feature
<222> LOCATION: (562)..(608)
<223> OTHER INFORMATION: T7 terminator
<220> FEATURE:
<221> NAME/KEY: misc_feature
<222> LOCATION: (934)..(951)
<223> OTHER INFORMATION: T7 promoter
<220> FEATURE:
<221> NAME/KEY: misc_feature
<222> LOCATION: (1023)..(1415)
<223> OTHER INFORMATION: MS2 bacteriophage coat protein
<220> FEATURE:
<221> NAME/KEY: misc_feature
<222> LOCATION: (1448)..(1494)
<223> OTHER INFORMATION: T7 terminator

<400> SEQUENCE: 1
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccgtactgc cgggcctctt      180 gcgggatgaa ttcagatctc gatcccgcga aattaatacg actcactata gggagaccac     240
aacggtttcc ctctagatca caagtttgta caaaaaagca ggctaagaag agatataca      300 tacgccggcc attcaaacat gaggattacc catgtattta aatacccatg tccaggcgcg     360
ctccgcgatc gcacgcggac aactactaca gggtttaaac ctttcggatt ataacatcac     420
atctaggcgc gcctgacgat caaccatacc agacggaccg aatacccggt ctgaacgagg     480
gcggccgcgg tacccaagaa gtacttagag ttaattaagg agttcaaaca tgaggatcac     540
ccatgtcgaa gctcccacac cctagcataa ccccttgggg cctctaaacg ggtcttgagg     600
ggttttttgc tgaaaggagg aactatatcc ggatatccac aggacgggtg tggtcgccat     660
gatcgcgtag tcgatagtgg ctccaagtag cgaagcgagc aggactgggc ggcgggcatg     720
```

```
catcgtccat tccgacagca tcgccagtca ctatggcgtg ctgctagcgc tatatgcgtt    780
gatgcaattt ctatgcgcac ccgttctcgg agcactgtcc gaccgctttg gccgccgccc    840
agtcctgctc gcttcgctac ttggagccac tatcgactac gcgatcatgg cgaccacacc    900
cgtcctgtgg atccagatct cgatcccgcg aaattaatac gactcactat agggagacca    960
caacggtttc cctctagatc acaagtttgt acaaaaaagc aggctaagaa ggagatatac   1020
atatggcgtc taactttacc caattcgttc tggttgataa cggcggtacg ggtgacgtta   1080
ccgtagctcc gtccaacttc gccaacggtg ttgcggaatg gattagctct aacagccgct   1140
ctcaggccta caaagtcacg tgctccgttc gtcagtctag cgcgcagaat cgcaaataca   1200
ccatcaaagt tgaagtaccg aaagtcgcaa cgcagaccgt aggcggcgta gaactcccag   1260
ttgcggcctg cgctcttac ctcaacatgg aactgactat tccgattttt gcgacgaact   1320
ccgactgcga actgattgtt aaggcaatgc agggcctgct gaaagacggt aatccgatcc   1380
catctgcaat cgctgctaac tctggcattt actaataagc ggacgcgctg ccaccgctga   1440
gcaataacta gcataacccc ttggggcctc taaacgggtc ttgaggggtt ttttgctgaa   1500
aggaggaact atatccggca tgcaccattc cttgcggcgg cggtgctcaa cggcctcaac   1560
ctactactgg gctgcttcct aatgcaggag tcgcataagg gagagcgtcg accgatgccc   1620
ttgagagcct tcaacccagt cagctccttc cggtgggcgc ggggcatgac tatcgtcgcc   1680
gcacttatga ctgtcttctt tatcatgcaa ctcgtaggac aggtgccggc agcgctctgg   1740
gtcattttcg gcgaggaccg ctttcgctgg agcgcgacga tgatcggcct gtcgcttgcg   1800
gtattcggaa tcttgcacgc cctcgctcaa gccttcgtca ctggtcccgc caccaaacgt   1860
ttcggcgaga gcaggccat tatcgccggc atggcggccg acgcgctggg ctacgtcttg   1920
ctggcgttcg cgacgcgagg ctggatggcc ttccccatta tgattcttct cgcttccggc   1980
ggcatcggga tgcccgcgtt gcaggccatg ctgtccaggc aggtagatga cgaccatcag   2040
ggacagcttc aaggatcgct cgcggctctt accagcctaa cttcgatcat tggaccgctg   2100
atcgtcacgg cgatttatgc cgcctcggcg agcacatgga acgggttggc atggattgta   2160
ggcgccgccc tataccttgt ctgcctcccc gcgttgcgtc gcggtgcatg gagccgggcc   2220
acctcgacct gaatggaagc cggcggcacc tcgctaacgg attcaccact ccaagaattg   2280
gagccaatca attcttgcgg agaactgtga atgcgcaaac caaccccttgg cagaacatat   2340 ccatcgcgtc cgccatctcc agcagccgca cgcggcgcat ctcgggcagc gttgggtcct   2400
ggccacgggt gcgcatgatc gtgctcctgt cgttgaggac ccggctaggc tggcggggtt   2460
gccttactgg ttagcagaat gaatcaccga tacgcgagcg aacgtgaagc gactgctgct   2520
gcaaaacgtc tgcgacctga gcaacaacat gaatggtctt cggtttccgt gtttcgtaaa   2580
gtctggaaac gcggaagtca gcgccctgca ccattatgtt ccggatctgc atcgcaggat   2640
gctgctggct accctgtgga acacctacat ctgtattaac gaagcgctgg cattgaccct   2700
gagtgatttt tctctggtcc cgccgcatcc ataccgccag ttgtttaccc tcacaacgtt   2760
ccagtaaccg gcatgttca tcatcagtaa cccgtatcgt gagcatcctc tctcgtttca   2820
tcggtatcat taccccatg aacagaaatc cccttacac ggaggcatca gtgaccaaac   2880
aggaaaaaac cgcccttaac atggcccgct ttatcagaag ccagacatta acgcttctgg   2940
agaaactcaa cgagctggac gcggatgaac aggcagacat ctgtgaatcg cttcacgacc   3000
acgctgatga gctttaccgc agctgcctcg cgcgtttcgg tgatgacggt gaaaacctct   3060
```

```
gacacatgca gctcccggag acggtcacag cttgtctgta agcggatgcc gggagcagac      3120
aagcccgtca gggcgcgtca gcgggtgttg gcgggtgtcg gggcgcagcc atgacccagt      3180
cacgtagcga tagcggagtg tatactggct taactatgcg gcatcagagc agattgtact      3240
gagagtgcac catatgcggt gtgaaatacc gcacagatgc gtaaggagaa ataccgcat       3300 caggcgctct tccgcttcct cgctcactga ctcgctgcgc tcggtcgttc ggctgcggcg      3360
agcggtatca gctcactcaa aggcggtaat acggttatcc acagaatcag gggataacgc      3420
aggaaagaac atgtgagcaa aaggccagca aaaggccagg aaccgtaaaa aggccgcgtt      3480
gctggcgttt ttccataggc tccgcccccc tgacgagcat cacaaaaatc gacgctcaag      3540
tcagaggtgg cgaaacccga caggactata agataccag gcgtttcccc ctggaagctc       3600
cctcgtgcgc tctcctgttc cgaccctgcc gcttaccgga tacctgtccg cctttctccc      3660
ttcgggaagc gtggcgcttt ctcatagctc acgctgtagg tatctcagtt cggtgtaggt      3720
cgttcgctcc aagctgggct gtgtgcacga accccccgtt cagcccgacc gctgcgcctt      3780
atccggtaac tatcgtcttg agtccaaccc ggtaagacac gacttatcgc cactggcagc      3840
agccactggt aacaggatta gcagagcgag gtatgtaggc ggtgctacag agttcttgaa      3900
gtggtggcct aactacggct acactagaag gacagtattt ggtatctgcg ctctgctgaa      3960
gccagttacc ttcggaaaaa gagttggtag ctcttgatcc ggcaaacaaa ccaccgctgg      4020
tagcggtggt ttttttgttt gcaagcagca gattacgcgc agaaaaaaag gatctcaaga      4080
agatcctttg atcttttcta cggggtctga cgctcagtgg aacgaaaact cacgttaagg      4140
gattttggtc atgagattat caaaaaggat cttcacctag atccttttaa attaaaaatg      4200
aagttttaaa tcaatctaaa gtatatatga gtaaacttgg tctgacagtt accaatgctt      4260
aatcagtgag gcacctatct cagcgatctg tctatttcgt tcatccatag ttgcctgact      4320
ccccgtcgtg tagataacta cgatacggga gggcttacca tctggcccca gtgctgcaat      4380
gataccgcga gacccacgct caccggctcc agatttatca gcaataaacc agccagccgg      4440
aagggccgag cgcagaagtg gtcctgcaac tttatccgcc tccatccagt ctattaattg      4500
ttgccgggaa gctagagtaa gtagttcgcc agttaatagt ttgcgcaacg ttgttgccat      4560
tgctgcaggc atcgtggtgt cacgctcgtc gtttggtatg gcttcattca gctccggttc      4620
ccaacgatca aggcgagtta catgatcccc catgttgtgc aaaaaagcgg ttagctcctt      4680
cggtcctccg atcgttgtca gaagtaagtt ggccgcagtg ttatcactca tggttatggc      4740
agcactgcat aattctctta ctgtcatgcc atccgtaaga tgcttttctg tgactggtga      4800
gtactcaacc aagtcattct gagaatagtg tatgcggcga ccgagttgct cttgcccggc      4860
gtcaacacgg gataataccg cgccacatag cagaacttta aaagtgctca tcattggaaa      4920
acgttcttcg gggcgaaaac tctcaaggat cttaccgctg ttgagatcca gttcgatgta      4980
acccactcgt gcacccaact gatcttcagc atcttttact ttcaccagcg tttctgggtg      5040
agcaaaaaca ggaaggcaaa atgccgcaaa aaagggaata agggcgacac ggaaatgttg      5100
aatactcata ctcttccttt ttcaatatta ttgaagcatt tatcagggtt attgtctcat      5160
gagcggatac atatttgaat gtatttagaa aaataaacaa ataggggttc cgcgcacatt      5220
tccccgaaaa gtgccacctg acgtctaaga aaccattatt atcatgacat taacctataa      5280
aaataggcgt atcacgaggc cctttcgtct tcaagaa                              5317
```

<210> SEQ ID NO 2
<211> LENGTH: 41

```
<212> TYPE: DNA
<213> ORGANISM: Artificial Sequence
<220> FEATURE:
<223> OTHER INFORMATION: PCR primer 1174

<400> SEQUENCE: 2
cattggcgat cgcgcacgag gttttctgt ctagtgagca g                   41

<210> SEQ ID NO 3
<211> LENGTH: 37
<212> TYPE: DNA
<213> ORGANISM: Artificial Sequence
<220> FEATURE:
<223> OTHER INFORMATION: PCR primer 1175

<400> SEQUENCE: 3
cattggttta aactcatccc agttggtgat gataccg                       37

<210> SEQ ID NO 4
<211> LENGTH: 200
<212> TYPE: DNA
<213> ORGANISM: Artificial Sequence
<220> FEATURE:
<223> OTHER INFORMATION: PCR primer 1213

<400> SEQUENCE: 4
cattggttta accctctag ctgctttaca aagtactggt tccctttcca gcgggatgct    60
ttatctaaac gcaatgagag aggtattcct caggccacat cgcttcctag ttccgctggg  120
atccatcgtt ggcggccgaa gccgccattc catagtgagt tctggcgcgc ctcatcccag  180
ttggtgatga taccgtgttc                                             200

<210> SEQ ID NO 5
<211> LENGTH: 37
<212> TYPE: DNA
<213> ORGANISM: Artificial Sequence
<220> FEATURE:
<223> OTHER INFORMATION: PCR primer 1203

<400> SEQUENCE: 5
cattgcggtc cggcacgagg tttttctgtc tagtgag                       37

<210> SEQ ID NO 6
<211> LENGTH: 5990
<212> TYPE: DNA
<213> ORGANISM: Artificial Sequence
<220> FEATURE:
<223> OTHER INFORMATION: plasmid pAPSE 10216
<220> FEATURE:
<221> NAME/KEY: misc_feature
<222> LOCATION: (213)..(230)
<223> OTHER INFORMATION: T7 promoter
<220> FEATURE:
<221> NAME/KEY: misc_feature
<222> LOCATION: (317)..(335)
<223> OTHER INFORMATION: MS2 bacteriophage PAC sequence
<220> FEATURE:
<221> NAME/KEY: misc_feature
<222> LOCATION: (365)..(372)
<223> OTHER INFORMATION: AsiSI restriction site
<220> FEATURE:
<221> NAME/KEY: misc_feature
<222> LOCATION: (373)..(666)
<223> OTHER INFORMATION: Antisense fragment of Leptinotarsa
      decemlineata strain Freeville actin mRNA, Genbank sequence ID:
      gb|KJ577616.1, nucleotides 46-261
<220> FEATURE:
<221> NAME/KEY: misc_feature
<222> LOCATION: (667)..(674)
```

```
<223> OTHER INFORMATION: PmeI restriction site
<220> FEATURE:
<221> NAME/KEY: misc_feature
<222> LOCATION: (675)..(824)
<223> OTHER INFORMATION: Loop
<220> FEATURE:
<221> NAME/KEY: misc_feature
<222> LOCATION: (825)..(832)
<223> OTHER INFORMATION: AscI restriction site
<220> FEATURE:
<221> NAME/KEY: misc_feature
<222> LOCATION: (833)..(1126)
<223> OTHER INFORMATION: Sense fragment of Leptinotarsa decemlineata
      strain Freeville actin mRNA,

```
ggcttcatct cctacgtatg agtccttttg tcccataccg accatgactc cttgatgcct      960
tgggcgaccg acgatcgagg ggaagacggc acggggtgcg tcatctcctg cgaaaccggc     1020
tttgcacata ccggatccat tgtctacgac aagagccgct acatcgtcgt cacacatgtt     1080
gtcttttgag gttggacact gctcactaga cagaaaaacc tcgtgccgga ccgaataccc     1140
ggtctgaacg agggcggccg cggtacccaa gaagtactta gagttaatta aggagttcaa     1200
acatgaggat cacccatgtc gaagctccca cacccctagca taacccccttg gggcctctaa    1260 acgggtcttg aggggttttt tgctgaaagg aggaactata tccggatatc cacaggacgg     1320
gtgtggtcgc catgatcgcg tagtcgatag tggctccaag tagcgaagcg agcaggactg     1380
ggcggcgggc atgcatcgtc cattccgaca gcatcgccag tcactatggc gtgctgctag     1440
cgctatatgc gttgatgcaa tttctatgcg cacccgttct cggagcactg tccgaccgct     1500
ttggccgccg cccagtcctg ctcgcttcgc tacttggagc cactatcgac tacgcgatca     1560
tggcgaccac acccgtcctg tggatccaga tctcgatccc gcgaaattaa tacgactcac     1620
tatagggaga ccacaacggt ttccctctag atcacaagtt tgtacaaaaa agcaggctaa     1680
gaaggagata tacatatggc gtctaacttt acccaattcg ttctggttga taacggcggt     1740
acgggtgacg ttaccgtagc tccgtccaac ttcgccaacg gtgttgcgga atggattagc     1800
tctaacagcc gctctcaggc ctacaaagtc acgtgctccg ttcgtcagtc tagcgcgcag     1860
aatcgcaaat acaccatcaa agttgaagta ccgaaagtcg caacgcagac cgtaggcggc     1920
gtagaactcc cagttgcggc ctggcgctct tacctcaaca tggaactgac tattccgatt     1980
tttgcgacga actccgactg cgaactgatt gttaaggcaa tgcagggcct gctgaaagac     2040
ggtaatccga tcccatctgc aatcgctgct aactctggca tttactaata agcggacgcg     2100
ctgccaccgc tgagcaataa ctagcataac cccttggggc ctctaaacgg gtcttgaggg     2160
gttttttgct gaaaggagga actatatccg gcatgcacca ttccttgcgg cggcggtgct     2220
caacggcctc aacctactac tgggctgctt cctaatgcag gagtcgcata agggagagcg     2280
tcgaccgatg cccttgagag ccttcaaccc agtcagctcc ttccggtggg cgcggggcat     2340
gactatcgtc gccgcactta tgactgtctt ctttatcatg caactcgtag acaggtgcc     2400 ggcagcgctc tgggtcattt tcggcgagga ccgctttcgc tggagcgcga cgatgatcgg     2460
cctgtcgctt gcggtattcg gaatcttgca cgccctcgct caagccttcg tcactggtcc     2520
cgccaccaaa cgtttcggcg agaagcaggc cattatcgcc ggcatggcgg ccgacgcgct     2580
gggctacgtc ttgctggcgt tcgcgacgcg aggctggatg gccttcccca ttatgattct     2640
tctcgcttcc ggcggcatcg ggatgcccgc gttgcaggcc atgctgtcca ggcaggtaga     2700
tgacgaccat cagggacagc ttcaaggatc gctcgcggct cttaccagcc taacttcgat     2760
cattggaccg ctgatcgtca cggcgattta tgccgcctcg gcgagcacat ggaacgggtt     2820
ggcatggatt gtaggcgccg ccctatacct tgtctgcctc cccgcgttgc gtcgcggtgc     2880
atggagccgg gccacctcga cctgaatgga agccggcggc acctcgctaa cggattcacc     2940
actccaagaa ttggagccaa tcaattcttg cggagaactg tgaatgcgca aaccaaccct     3000
tggcagaaca tatccatcgc gtccgccatc tccagcagcc gcacgcggcg catctcgggc     3060
agcgttgggt cctggccacg ggtgcgcatg atcgtgctcc tgtcgttgag gacccggcta     3120
ggctggcggg gttgccttac tggttagcag aatgaatcac cgatacgcga gcgaacgtga     3180
agcgactgct gctgcaaaac gtctgcgacc tgagcaacaa catgaatggt cttcggtttc     3240
```

```
cgtgtttcgt aaagtctgga aacgcggaag tcagcgccct gcaccattat gttccggatc    3300
tgcatcgcag gatgctgctg gctaccctgt ggaacaccta catctgtatt aacgaagcgc    3360
tggcattgac cctgagtgat ttttctctgg tcccgccgca tccataccgc cagttgttta    3420
ccctcacaac gttccagtaa ccgggcatgt tcatcatcag taacccgtat cgtgagcatc    3480
ctctctcgtt tcatcggtat cattaccccc atgaacagaa atcccccctta cacggaggca    3540 tcagtgacca acaggaaaa aaccgcccctt aacatggccc gctttatcag aagccagaca    3600
ttaacgcttc tggagaaact caacgagctg gacgcggatg aacaggcaga catctgtgaa    3660
tcgcttcacg accacgctga tgagctttac cgcagctgcc tcgcgcgttt cggtgatgac    3720
ggtgaaaacc tctgacacat gcagctcccg gagacggtca cagcttgtct gtaagcggat    3780
gccgggagca gacaagcccg tcagggcgcg tcagcgggtg ttggcgggtg tcggggcgca    3840
gccatgaccc agtcacgtag cgatagcgga gtgtatactg gcttaactat gcggcatcag    3900
agcagattgt actgagagtg caccatatgc ggtgtgaaat accgcacaga tgcgtaagga    3960
gaaaataccg catcaggcgc tcttccgctt cctcgctcac tgactcgctg cgctcggtcg    4020
ttcggctgcg gcgagcggta tcagctcact caaaggcggt aatacggtta tccacagaat    4080
caggggataa cgcaggaaag aacatgtgag caaaaggcca gcaaaaggcc aggaaccgta    4140
aaaaggccgc gttgctggcg ttttttccata ggctccgccc ccctgacgag catcacaaaa    4200
atcgacgctc aagtcagagg tggcgaaacc cgacaggact ataaagatac caggcgtttc    4260
cccctggaag ctccctcgtg cgctctcctg ttccgaccct gccgcttacc ggatacctgt    4320
ccgcctttct cccttcggga agcgtggcgc tttctcatag ctcacgctgt aggtatctca    4380
gttcggtgta ggtcgttcgc tccaagctgg gctgtgtgca cgaaccccccc gttcagcccg    4440 accgctgcgc cttatccggt aactatcgtc ttgagtccaa cccggtaaga cacgacttat    4500
cgccactggc agcagccact ggtaacagga ttagcagagc gaggtatgta ggcggtgcta    4560
cagagttctt gaagtggtgg cctaactacg gctacactag aaggacagta tttggtatct    4620
gcgctctgct gaagccagtt accttcggaa aaagagttgg tagctcttga tccggcaaac    4680
aaaccaccgc tggtagcggt ggtttttttg tttgcaagca gcagattacg cgcagaaaaa    4740
aaggatctca agaagatcct ttgatctttt ctacggggtc tgacgctcag tggaacgaaa    4800
actcacgtta agggattttg gtcatgagat tatcaaaaag gatcttcacc tagatccttt    4860
taaattaaaa atgaagtttt aaatcaatct aaagtatata tgagtaaact tggtctgaca    4920
gttaccaatg cttaatcagt gaggcaccta tctcagcgat ctgtctattt cgttcatcca    4980
tagttgcctg actccccgtc gtgtagataa ctacgatacg ggagggctta ccatctggcc    5040
ccagtgctgc aatgataccg cgagacccac gctcaccggc tccagattta tcagcaataa    5100
accagccagc cggaagggcc gagcgcagaa gtggtcctgc aactttatcc gcctccatcc    5160
agtctattaa ttgttgccgg gaagctagag taagtagttc gccagttaat agttgcgca    5220 acgttgttgc cattgctgca ggcatcgtgg tgtcacgctc gtcgtttggt atggcttcat    5280
tcagctccgg ttcccaacga tcaaggcgag ttacatgatc ccccatgttg tgcaaaaaag    5340
cggttagctc cttcggtcct ccgatcgttg tcagaagtaa gttggccgca gtgttatcac    5400
tcatggttat ggcagcactg cataattctc ttactgtcat gccatccgta agatgctttt    5460
ctgtgactgg tgagtactca accaagtcat tctgagaata gtgtatgcgg cgaccgagtt    5520
gctcttgccc ggcgtcaaca cgggataata ccgcgccaca tagcagaact ttaaaagtgc    5580
tcatcattgg aaaacgttct tcggggcgaa aactctcaag gatcttaccg ctgttgagat    5640
```

```
ccagttcgat gtaacccact cgtgcaccca actgatcttc agcatctttt actttcacca   5700
gcgtttctgg gtgagcaaaa acaggaaggc aaaatgccgc aaaaaaggga ataagggcga   5760
cacggaaatg ttgaatactc atactcttcc tttttcaata ttattgaagc atttatcagg   5820
gttattgtct catgagcgga tacatatttg aatgtattta gaaaaataaa caaatagggg   5880
ttccgcgcac atttccccga aaagtgccac ctgacgtcta agaaaccatt attatcatga   5940
cattaaccta taaaaatagg cgtatcacga ggccctttcg tcttcaagaa              5990

<210> SEQ ID NO 7
<211> LENGTH: 37
<212> TYPE: DNA
<213> ORGANISM: Artificial Sequence
<220> FEATURE:
<223> OTHER INFORMATION: PCR primer 1176

<400> SEQUENCE: 7
cattggcgat cgctcatccc agttggtgat gataccg                              37

<210> SEQ ID NO 8
<211> LENGTH: 38
<212> TYPE: DNA
<213> ORGANISM: Artificial Sequence
<220> FEATURE:
<223> OTHER INFORMATION: PCR primer 1177

<400> SEQUENCE: 8
cattggttta aacgcacgag gtttttctgt ctagtgag                             38

<210> SEQ ID NO 9
<211> LENGTH: 5591
<212> TYPE: DNA
<213> ORGANISM: Artificial Sequence
<220> FEATURE:
<223> OTHER INFORMATION: plasmid pAPSE 10190
<220> FEATURE:
<221> NAME/KEY: misc_feature
<222> LOCATION: (213)..(230)
<223> OTHER INFORMATION: T7 promoter
<220> FEATURE:
<221> NAME/KEY: misc_feature
<222> LOCATION: (317)..(335)
<223> OTHER INFORMATION: MS2 bacteriophage PAC sequence
<220> FEATURE:
<221> NAME/KEY: misc_feature
<222> LOCATION: (365)..(372)
<223> OTHER INFORMATION: AsiSI restriction site
<220> FEATURE:
<221> NAME/KEY: misc_feature
<222> LOCATION: (373)..(666)
<223> OTHER INFORMATION: antisense  fragment of  Leptinotarsa
      decemlineata strain Freeville actin mRNA, Genbank sequence ID:
      gb|KJ577616.1, nucleotides 46-261
<220> FEATURE:
<221> NAME/KEY: misc_feature
<222> LOCATION: (667)..(674)
<223> OTHER INFORMATION: PmeI restriction site
<220> FEATURE:
<221> NAME/KEY: misc_feature
<222> LOCATION: (700)..(707)
<223> OTHER INFORMATION: AscI restriction site
<220> FEATURE:
<221> NAME/KEY: misc_feature
<222> LOCATION: (728)..(7734)
<223> OTHER INFORMATION: RsrII restriction site
<220> FEATURE:
<221> NAME/KEY: misc_feature
<222> LOCATION: (755)..(762)
<223> OTHER INFORMATION: NotI restriction site
<220> FEATURE:
```

```
<221> NAME/KEY: misc_feature
<222> LOCATION: (785)..(792)
<223> OTHER INFORMATION: PacI restriction site
<220> FEATURE:
<221> NAME/KEY: misc_feature
<222> LOCATION: (802)..(820)
<223> OTHER INFORMATION: MS2 bacteriophage C-PAC sequence
<220> FEATURE:
<221> NAME/KEY: misc_feature
<222> LOCATION: (836)..(882)
<223> OTHER INFORMATION: T7 terminator
<220> FEATURE:
<221> NAME/KEY: misc_feature
<222> LOCATION: (1208)..(1225)
<223> OTHER INFORMATION: T7 promoter
<220> FEATURE:
<221> NAME/KEY: misc_feature
<222> LOCATION: (1297)..(1692)
<223> OTHER INFORMATION: MS2 bacteriophage coat protein
<220> FEATURE:
<221> NAME/KEY: misc_feature
<222> LOCATION: (1722)..(1768)
<223> OTHER INFORMATION: T7 terminator

<400> SEQUENCE: 9
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300 tacgccggcc attcaaacat gaggattacc catgtattta atacccatg tccaggcgcg     360 ctccgcgatc gctcatccca gttggtgatg ataccgtgtt cgatggggta tttcagggtg     420
aggatacctc ttttgctttg ggcttcatct cctacgtatg agtccttttg tcccataccg     480
accatgactc cttgatgcct tgggcgaccg acgatcgagg ggaagacggc acggggtgcg     540
tcatctcctg cgaaaccggc tttgcacata ccggatccat tgtctacgac aagagccgct     600
acatcgtcgt cacacatgtt gtcttttgag gttggacact gctcactaga cagaaaaacc     660
tcgtgcgttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca acatgagga tcacccatgt cgaagctccc acaccctagc     840
ataacccctt ggggcctcta acgggtctt gagggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcatcgt ccattccgac agcatcgcca    1020
gtcactatgg cgtgctgcta gcgctatatg cgttgatgca atttctatgc gcacccgttc    1080
tcggagcact gtccgaccgc tttggccgcc gcccagtcct gctcgcttcg ctacttggag    1140
ccactatcga ctacgcgatc atggcgacca caccgtcct gtggatccag atctcgatcc    1200
cgcgaaatta atacgactca ctatagggag accacaacgg tttccctcta gatcacaagt    1260
ttgtacaaaa aagcaggcta agaaggagat atacatatgg cgtctaactt tacccaattc    1320
gttctggttg ataacggcgg tacgggtgac gttaccgtag ctccgtccaa cttcgccaac    1380
ggtgttgcgg aatggattag ctctaacagc cgctctcagg cctacaaagt cacgtgctcc    1440
gttcgtcagt ctagcgcgca gaatcgcaaa tacaccatca agttgaagt accgaaagtc    1500 gcaacgcaga ccgtaggcgg cgtagaactc ccagttgcgg cctggcgctc ttacctcaac    1560
atggaactga ctattccgat ttttgcgacg aactccgact gcgaactgat tgttaaggca    1620
```

-continued

```
atgcagggcc tgctgaaaga cggtaatccg atcccatctg caatcgctgc taactctggc    1680
atttactaat aagcggacgc gctgccaccg ctgagcaata actagcataa cccttgggg      1740
cctctaaacg ggtcttgagg ggttttttgc tgaaaggagg aactatatcc ggcatgcacc    1800
attccttgcg gcggcggtgc tcaacggcct caacctacta ctgggctgct tcctaatgca    1860
ggagtcgcat aagggagagc gtcgaccgat gcccttgaga gccttcaacc cagtcagctc    1920
cttccggtgg gcgcggggca tgactatcgt cgccgcactt atgactgtct tctttatcat    1980
gcaactcgta ggacaggtgc cggcagcgct ctgggtcatt ttcggcgagg accgctttcg    2040
ctggagcgcg acgatgatcg gcctgtcgct tgcggtattc ggaatcttgc acgccctcgc    2100
tcaagccttc gtcactggtc ccgccaccaa acgtttcggc gagaagcagg ccattatcgc    2160
cggcatggcg gccgacgcgc tgggctacgt cttgctggcg ttcgcgacgc gaggctggat    2220
ggccttcccc attatgattc ttctcgcttc cggcggcatc gggatgcccg cgttgcaggc    2280
catgctgtcc aggcaggtag atgacgacca tcagggacag cttcaaggat cgctcgcggc    2340
tcttaccagc ctaacttcga tcattggacc gctgatcgtc acggcgattt atgccgcctc    2400
ggcgagcaca tggaacgggt tggcatggat tgtaggcgcc gccctatacc ttgtctgcct    2460
ccccgcgttg cgtcgcggtg catggagccg ggccacctcg acctgaatgg aagccggcgg    2520
cacctcgcta acggattcac cactccaaga attggagcca atcaattctt gcggagaact    2580
gtgaatgcgc aaaccaaccc ttggcagaac atatccatcg cgtccgccat ctccagcagc    2640
cgcacgcggc gcatctcggg cagcgttggg tcctggccac gggtgcgcat gatcgtgctc    2700
ctgtcgttga ggacccggct aggctggcgg ggttgcctta ctggttagca gaatgaatca    2760
ccgatacgcg agcgaacgtg aagcgactgc tgctgcaaaa cgtctgcgac ctgagcaaca    2820
acatgaatgg tcttcggttt ccgtgtttcg taaagtctgg aaacgcggaa gtcagcgccc    2880
tgcaccatta tgttccggat ctgcatcgca ggatgctgct ggctaccctg tggaacacct    2940
acatctgtat taacgaagcg ctggcattga ccctgagtga ttttttctctg gtcccgccgc    3000
atccataccg ccagttgttt accctcacaa cgttccagta accgggcatg ttcatcatca    3060
gtaacccgta tcgtgagcat cctctctcgt ttcatcggta tcattacccc catgaacaga    3120
aatccccctt acacggaggc atcagtgacc aaacaggaaa aaaccgccct aacatggcc     3180
cgctttatca gaagccagac attaacgctt ctggagaaac tcaacgagct ggacgcggat    3240
gaacaggcag acatctgtga atcgcttcac gaccacgctg atgagcttta ccgcagctgc    3300
ctcgcgcgtt tcggtgatga cggtgaaaac ctctgacaca tgcagctccc ggagacggtc    3360
acagcttgtc tgtaagcgga tgccgggagc agacaagccc gtcagggcgc gtcagcgggt    3420
gttggcgggt gtcggggcgc agccatgacc cagtcacgta gcgatagcgg agtgtatact    3480
ggcttaacta tgcggcatca gagcagattg tactgagagt gcaccatatg cggtgtgaaa    3540
taccgcacag atgcgtaagg agaaaatacc gcatcaggcg ctcttccgct tcctcgctca    3600
ctgactcgct gcgctcggtc gttcggctgc ggcgagcggt atcagctcac tcaaaggcgg    3660
taatacggtt atccacagaa tcaggggata acgcaggaaa gaacatgtga gcaaaaggcc    3720
agcaaaaggc caggaaccgt aaaaaggccg cgttgctggc gttttccat aggctccgcc     3780
cccctgacga gcatcacaaa aatcgacgct caagtcagag gtggcgaaac ccgacaggac    3840
tataaagata ccaggcgttt ccccctggaa gctccctcgt gcgctctcct gttccgaccc    3900
tgccgcttac cggatacctg tccgcctttc tcccttcggg aagcgtggcg ctttctcata    3960
```

-continued

| | |
|---|---|
| gctcacgctg taggtatctc agttcggtgt aggtcgttcg ctccaagctg ggctgtgtgc | 4020 |
| acgaaccccc cgttcagccc gaccgctgcg ccttatccgg taactatcgt cttgagtcca | 4080 |
| acccggtaag acacgactta tcgccactgg cagcagccac tggtaacagg attagcagag | 4140 |
| cgaggtatgt aggcggtgct acagagttct tgaagtggtg gcctaactac ggctacacta | 4200 |
| gaaggacagt atttggtatc tgcgctctgc tgaagccagt taccttcgga aaaagagttg | 4260 |
| gtagctcttg atccggcaaa caaaccaccg ctggtagcgg tggttttttt gtttgcaagc | 4320 |
| agcagattac gcgcagaaaa aaaggatctc aagaagatcc tttgatcttt tctacggggt | 4380 |
| ctgacgctca gtggaacgaa aactcacgtt aagggatttt ggtcatgaga ttatcaaaaa | 4440 |
| ggatcttcac ctagatcctt ttaaattaaa aatgaagttt taaatcaatc taaagtatat | 4500 |
| atgagtaaac ttggtctgac agttaccaat gcttaatcag tgaggcacct atctcagcga | 4560 |
| tctgtctatt tcgttcatcc atagttgcct gactccccgt cgtgtagata actacgatac | 4620 |
| gggagggctt accatctggc cccagtgctg caatgatacc gcgagaccca cgctcaccgg | 4680 |
| ctccagattt atcagcaata aaccagccag ccggaagggc cgagcgcaga agtggtcctg | 4740 |
| caactttatc cgcctccatc cagtctatta attgttgccg ggaagctaga gtaagtagtt | 4800 |
| cgccagttaa tagtttgcgc aacgttgttg ccattgctgc aggcatcgtg gtgtcacgct | 4860 |
| cgtcgtttgg tatggcttca ttcagctccg gttcccaacg atcaaggcga gttacatgat | 4920 |
| cccccatgtt gtgcaaaaaa gcggttagct ccttcggtcc tccgatcgtt gtcagaagta | 4980 |
| agttggccgc agtgttatca ctcatggtta tggcagcact gcataattct cttactgtca | 5040 |
| tgccatccgt aagatgcttt tctgtgactg gtgagtactc aaccaagtca ttctgagaat | 5100 |
| agtgtatgcg gcgaccgagt tgctcttgcc cggcgtcaac acgggataat accgcgccac | 5160 |
| atagcagaac tttaaaagtg ctcatcattg gaaaacgttc ttcggggcga aaactctcaa | 5220 |
| ggatcttacc gctgttgaga tccagttcga tgtaacccac tcgtgcaccc aactgatctt | 5280 |
| cagcatcttt tactttcacc agcgtttctg ggtgagcaaa aacaggaagg caaaatgccg | 5340 |
| caaaaaaggg aataagggcg acacggaaat gttgaatact catactcttc ctttttcaat | 5400 |
| attattgaag catttatcag ggttattgtc tcatgagcgg atacatattt gaatgtattt | 5460 |
| agaaaaataa acaaataggg gttccgcgca catttccccg aaaagtgcca cctgacgtct | 5520 |
| aagaaaccat tattatcatg acattaacct ataaaaatag gcgtatcacg aggccctttc | 5580 |
| gtcttcaaga a | 5591 |

What is claimed is:

1. A method for controlling target insects comprising, transforming a bacterium with a first DNA sequence comprising a gene encoding a levivirus Qβ capsid protein or a levivirus MS2 capsid protein and a second DNA sequence encoding an RNA transcript comprising at least one bacteriophage pac sequence coupled to an RNAi precursor sequence, inducing the bacterium to express the first and second DNA sequences, isolating virus-like-particles (VLPs) consisting of the capsid protein enclosing the RNAi precursor from the bacterium, and contacting the isolated VLPs with the target insects, wherein the target insect comprises a Coleopteran insect or a Lepidopteran insect.

2. The method of claim 1, wherein the RNAi precursor forms an siRNA.

3. The method of claim 1, wherein the RNAi precursor forms an antisense RNA.

4. The method of claim 1, wherein the first DNA sequence and second DNA sequence are on separate episomes.

5. The method of claim 1, wherein the first DNA sequence and the second DNA sequence are on the same episome.

6. The method of claim 1, wherein one of the first DNA sequence and the second DNA sequence is integrated into the bacterial host chromosome.

7. The method of claim 1, wherein both the first DNA sequence and the second DNA sequence are integrated into the bacterial host chromosome.

8. The method of claim 1, wherein the bacterium is *Escherichia coli*.

9. The method of claim 1, wherein the target insect comprises a Coleopteran insect.

10. The method of claim 9 wherein the target insect comprises Colorado potato beetle.

* * * * *